(12) United States Patent
He et al.

(10) Patent No.: US 10,095,910 B2
(45) Date of Patent: Oct. 9, 2018

(54) FINGERPRINT IDENTIFICATION CIRCUIT, TOUCH APPARATUS AND FINGERPRINT IDENTIFICATION METHOD

(71) Applicants: BOE TECHNOLOGY GROUP CO., LTD., Beijing (CN); CHENGDU BOE OPTOELECTRONICS TECHNOLOGY CO., LTD., Sichuan (CN)

(72) Inventors: Xiaoxiang He, Beijing (CN); Xiaojing Qi, Beijing (CN)

(73) Assignees: BOE TECHNOLOGY GROUP CO., LTD., Beijing (CN); CHENGDU BOE OPTOELECTRONICS TECHNOLOGY CO., LTD., Chengdu, Sichuan (CN)

( * ) Notice: Subject to any disclaimer, the term of this patent is extended or adjusted under 35 U.S.C. 154(b) by 0 days.

(21) Appl. No.: 15/562,570

(22) PCT Filed: Feb. 23, 2017

(86) PCT No.: PCT/CN2017/074551
§ 371 (c)(1),
(2) Date: Sep. 28, 2017

(87) PCT Pub. No.: WO2017/197945
PCT Pub. Date: Nov. 23, 2017

(65) Prior Publication Data
US 2018/0211080 A1    Jul. 26, 2018

(30) Foreign Application Priority Data
May 20, 2016  (CN) .......................... 2016 1 0342252

(51) Int. Cl.
*G06K 9/00*  (2006.01)
*G06F 3/044*  (2006.01)
(Continued)

(52) U.S. Cl.
CPC .......... *G06K 9/0002* (2013.01); *A61B 5/1172* (2013.01); *G06F 3/044* (2013.01);
(Continued)

(58) Field of Classification Search
CPC ............. A61B 5/1172; G06K 9/00013; G06K 9/0002; G06K 9/0004; G06K 9/0012; G06K 9/00046; G06K 19/0718
See application file for complete search history.

(56) References Cited

U.S. PATENT DOCUMENTS 9,158,958 B2 * 10/2015 Wickboldt .......... G06K 9/00026
9,779,280 B2 * 10/2017 Benkley, III ....... G06K 9/00033
(Continued)

FOREIGN PATENT DOCUMENTS

CN    104077565 A    10/2014
CN    104112120 A    10/2014
(Continued)

OTHER PUBLICATIONS

International Search Report dated May 31, 2017 corresponding to application No. PCT/CN2017/074551.

*Primary Examiner* — Utpal Shah
(74) *Attorney, Agent, or Firm* — Nath, Goldberg & Meyer; Joshua B. Goldberg

(57) ABSTRACT

A fingerprint identification circuit comprises multiple reading sub-circuits, and multiple fingerprint identification sub-circuits each column of fingerprint identification sub-circuits are connected with one reading sub-circuit, each fingerprint identification sub-circuit comprises a writing sub-circuit, a sensing sub-circuit and a output sub-circuit, the writing sub-circuit is connected with a scan signal input terminal; the sensing sub-circuit senses a fingerprint and transmits a sensing signal to the output sub-circuit; the output sub-circuit outputs the sensing signal upon the writing sub- (Continued)

circuit is turned off each fingerprint identification sub-circuit further comprises: a converting and amplifying sub-circuit provided between the sensing sub-circuit and the output sub-circuit, for converting the sensing signal into a current signal, amplifying the current signal and outputting it to the output sub-circuit, the reading sub-circuit is connected with the output sub-circuit for reading the sensing signal and converting the current signal into a voltage signal to output.

20 Claims, 4 Drawing Sheets

(51) Int. Cl.
*G06K 19/07* (2006.01)
*A61B 5/1172* (2016.01)
(52) U.S. Cl.
CPC ....... *G06K 9/0004* (2013.01); *G06K 9/00013* (2013.01); *G06K 9/00087* (2013.01); *G06K 19/0718* (2013.01)

(56) References Cited

U.S. PATENT DOCUMENTS

| | | | | |
|---|---|---|---|---|
| 9,823,794 | B2* | 11/2017 | Cho | G06F 3/044 |
| 2006/0158202 | A1* | 7/2006 | Umeda | G06K 9/0002 |
| | | | | 324/686 |
| 2007/0024546 | A1* | 2/2007 | Jang | G06K 9/0002 |
| | | | | 345/78 |
| 2008/0043119 | A1* | 2/2008 | Mabuchi | H04N 5/235 |
| | | | | 348/231.99 |
| 2009/0206849 | A1* | 8/2009 | Chuang | G06K 9/0002 |
| | | | | 324/686 |
| 2010/0073266 | A1* | 3/2010 | Na | G09G 3/3233 |
| | | | | 345/76 |
| 2010/0098303 | A1* | 4/2010 | Chen | G06K 9/0002 |
| | | | | 382/124 |
| 2010/0289784 | A1* | 11/2010 | Fujioka | G02F 1/13338 |
| | | | | 345/207 |
| 2013/0265137 | A1 | 10/2013 | Nelson et al. | |
| 2015/0348504 | A1* | 12/2015 | Sakariya | G09G 3/3233 |
| | | | | 345/206 |
| 2016/0086044 | A1* | 3/2016 | Yu | G06K 9/0004 |
| | | | | 250/208.1 |
| 2016/0180775 | A1* | 6/2016 | Kim | G09G 3/3233 |
| | | | | 345/205 |

FOREIGN PATENT DOCUMENTS

| | | |
|---|---|---|
| CN | 104155785 A | 11/2014 |
| CN | 104282265 A | 1/2015 |
| CN | 105426865 A | 3/2016 |
| CN | 105447439 A | 3/2016 |
| CN | 106056047 A | 10/2016 |

* cited by examiner

FINGERPRINT IDENTIFICATION CIRCUIT, TOUCH APPARATUS AND FINGERPRINT IDENTIFICATION METHOD

CROSS-REFERENCE TO RELATED APPLICATION

This is a National Phase Application filed under 35 U.S.C. 371 as a national stage of PCT/CN2017/074551, filed Feb. 23, 2017, an application claiming the benefit of Chinese Application No. 201610342252.1, filed May 20, 2016, the content of each of which is hereby incorporated by reference in its entirety.

TECHNICAL FIELD

The present disclosure relates to the field of fingerprint identification technology, and particularly, to a fingerprint identification circuit, a touch apparatus and a fingerprint identification method.

BACKGROUND ART

In recent years, with the popularization of electronic products such as mobile phones with a fingerprint-identification-unlocking function, fingerprint identification technology has been pushed into a new application era. The process of fingerprint identification in an electronic product is usually controlled by a fingerprint identification circuit.

FIG. 1 shows a structural diagram of a fingerprint identification circuit in the prior art, as shown in FIG. 1, the fingerprint identification circuit usually comprises a plurality of sensing electrodes 10 arranged in rows and columns, a plurality of scanning lines G (for example G1, G2, G3 and G4 in FIG. 1), a plurality of detection signal writing lines X (for example, X1, X2, X3 and X4 in FIG. 1) and a plurality of TFT switches 11 corresponding to the sensing electrodes 10.

Operation process of a first row of sensing electrodes in the fingerprint identification circuit shown in FIG. 1 will be described in detail below, and the operation process specifically includes the following stages.

(a) a detection signal writing stage: applying a driving voltage to the scanning line G1, so that the first row of TFT switches 11 are turned on, at the same time, writing a detection signal to each of the sensing electrodes 10 in the first row through the detection signal writing lines X1-X4 respectively.

(b) a fingerprint sensing stage: when no fingerprint texture sensing occurs, on a basis of capacitances generated by the sensing electrodes 10, each of the sensing electrodes 10 in the first row has a same potential, as shown by D1-D4 in FIG. 2a; when the sensing electrodes 10 are touched by a finger, since the fingerprint texture includes two morphologies consisting of peaks and valleys and a distance between a peak and the sensing electrode 10 is different from that between a valley and the sensing electrode 10, therefore, the influence of the peak on the capacitance of the sensing electrode 10 corresponding thereto is different from that of the valley on the capacitance of the sensing electrode 10 corresponding thereto, that is, the peak and the valley have different influence on the potential of the sensing electrode 10 corresponding thereto respectively, and when the fingerprint texture sensing occurs, potentials of the sensing electrodes 10 in the first row become different, as shown in FIG. 2b.

(c) a signal reading stage: each of the detection signal writing lines X is connected to a reading sub-circuit 12, as shown in FIG. 2c, the reading sub-circuit 12 is configured to read a sensing signal generated in the sensing electrode 10 after the fingerprint texture is sensed and process the sensing signal.

(d) a comparison process stage: comparing the detection signal written in the step (a) with the sensing signal read in the step (e), and determining whether the fingerprint texture corresponding to a position where each of the sensing electrodes 10 is located is a peak or a valley based on the difference obtained by the comparison.

And so forth, the above (a)~(d) are repeated, a second row of sensing electrodes, a third row of sensing electrodes, till to the last row of sensing electrodes are scanned in turn, so as to determine whether the fingerprint texture corresponding to a position where each of the sensing electrodes 10 of the overall fingerprint identification circuit is located is a peak or a valley.

However, the existing fingerprint identification circuit has the following problems in practical applications: the fingerprint identification is time-consuming and low accuracy.

SUMMARY

In view of at least one of the above problems in the prior art, the preset disclosure provides a fingerprint identification circuit, a touch apparatus and a fingerprint identification method, which can increase the accuracy of the fingerprint identification.

To solve one of the above problems, in one aspect, this disclosure provides a fingerprint identification circuit comprising a plurality of reading sub-circuits and a plurality of fingerprint identification sub-circuits arranged in rows and columns, wherein each column of fingerprint identification sub-circuits are connected with one reading sub-circuit, each of the fingerprint identification sub-circuits comprises a writing sub-circuit, a sensing sub-circuit and a output sub-circuit connected in sequence, a control terminal of the writing sub-circuit is connected with a scan signal input terminal and is turned on upon an active signal is input to the scan signal input terminal so as to write a detection signal to the sensing sub-circuit; the sensing sub-circuit senses a fingerprint and transmits the obtained sensing signal to the output sub-circuit, the output sub-circuit is turned on and outputs the sensing signal upon the writing sub-circuit is turned off, and is turned off upon the writing sub-circuit is turned on, and wherein each of the fingerprint identification sub-circuits further comprising:

a converting and amplifying sub-circuit, which is provided between the sensing sub-circuit and the output sub-circuit, for converting the sensing signal output from the sensing sub-circuit into a current signal, amplifying the current signal by a preset multiple and then outputting it to the output sub-circuit, wherein the reading sub-circuit is connected with an output terminal of the output sub-circuit, and is configured to read the sensing signal output from the output sub-circuit and convert the current signal into a voltage signal to output.

Optionally, each of the fingerprint identification sub-circuits further comprises a reset sub-circuit, which is provided between an output terminal of the converting and amplifying sub-circuit and an input terminal of the output sub-circuit, and is turned on upon the writing sub-circuit is turned on so as to reset the input terminal of the output sub-circuit to a low level.

Optionally, a control terminal of an output sub-circuit of one fingerprint identification sub-circuit is connected with a control terminal of a writing sub-circuit of another fingerprint identification sub-circuit in a same column and next row with respect to the one fingerprint identification sub-circuit, so that the output sub-circuit of the one fingerprint identification sub-circuit and the writing sub-circuit of the another fingerprint identification sub-circuit are turned on or turned off simultaneously.

Optionally, control terminals of the writing sub-circuits of the fingerprint identification sub-circuits in a same row are connected to a same scan signal input terminal, so that the writing sub-circuits of the fingerprint identification sub-circuits in a same row are turned on simultaneously upon an active signal is applied to the scan signal input terminal, and input terminals of the writing sub-circuits of the fingerprint identification sub-circuits in a same column are connected with a same signal line.

Optionally, each of the reading sub-circuits comprises:
an operation amplifier, an inverse input terminal of which is connected with the output terminal of the output sub-circuit, wherein a pure resistance sub-circuit is connected between the inverse input terminal and an output terminal of the operation amplifier.

Optionally, the writing sub-circuit comprises: a first transistor, a gate of which is configured as a control terminal of the writing sub-circuit for controlling on or off of the writing sub-circuit, a first pole of which is configured as an input terminal of the writing sub-circuit, and a second pole of which is configured as an output terminal of the writing sub-circuit.

Optionally, the sensing sub-circuit comprises: a first electrode and a second electrode provided oppositely, wherein
the first electrode is connected with the writing sub-circuit and the converting and amplifying sub-circuit respectively;
the second electrode is connected with a control signal terminal, wherein the control signal terminal is configured to input a control signal to adjust the preset multiple of the converting and amplifying sub-circuit.

Optionally, the converting and amplifying sub-circuit comprises: a second transistor, a gate of which is configured as an input terminal of the converting and amplifying sub-circuit, a first electrode of which is connected with a first level input terminal, and a second electrode of which is configured as an output terminal of the converting and amplifying sub-circuit.

Optionally, the output sub-circuit comprises a third transistor, a gate of which is configured as a control terminal of the output sub-circuit for controlling on or off of the output sub-circuit; a first electrode of which is configured as a signal input terminal of the output sub-circuit and is connected with the signal output terminal of the converting and amplifying sub-circuit; and a second electrode of which is configured as an output terminal of the output sub-circuit.

Optionally, the reset sub-circuit comprises a fourth transistor, a gate of which is configured as a control terminal of the reset sub-circuit for controlling on or off of the reset sub-circuit; a first electrode of which is connected with a second level input terminal; and a second electrode of which is configured as an output terminal of the reset sub-circuit and is connected to the input terminal of the output sub-circuit.

According to a second aspect, this disclosure provides a touch apparatus comprising a fingerprint identification circuit described as above.

According to a third aspect, this disclosure provides a fingerprint identification method by using the above fingerprint identification circuit, the fingerprint identification method comprises:

turning on a writing sub-circuit of a fingerprint identification sub-circuit to write a detection signal to a sensing sub-circuit of the fingerprint identification sub-circuit, and turning off the output sub-circuit of the fingerprint identification sub-circuit simultaneously;

after the writing sub-circuit completes the writing of the detection signal, the sensing sub-circuit senses a fingerprint, generates a sensing signal, and converts the sensing signal into a current signal and amplifies it by a preset multiple, and turns an output sub-circuit connected with the sensing sub-circuit on, the output sub-circuit, after being turned on, outputs the sensing signal sensed by the sensing sub-circuit; and reading, by the reading sub-circuit, the sensing signal output by the output sub-circuit and converting the current signal into a voltage signal to output.

Optionally, this method further comprises: resetting the input terminal of the output sub-circuit of the fingerprint identification sub-circuit to a low level upon the writing sub-circuit of the fingerprint identification sub-circuit writes the detection signal.

Optionally, this method further comprises: turning on a writing sub-circuit of another fingerprint identification sub-circuit in a same column and next row with respect to the fingerprint identification sub-circuit, while the output sub-circuit of the fingerprint identification sub-circuit is turned on.

BRIEF DESCRIPTION OF THE DRAWINGS

FIG. 3b is a specific circuit diagram of a fingerprint identification sub-circuit shown in FIG. 3a;

DETAILED DESCRIPTION OF THE EMBODIMENTS

In order to make a person skilled in the art understand solutions of this disclosure better, a fingerprint identification circuit, a touch apparatus and a fingerprint identification method provided by this disclosure will be described in detail below in conjunction with the accompanying drawings.

First Embodiment

Figure 3A:
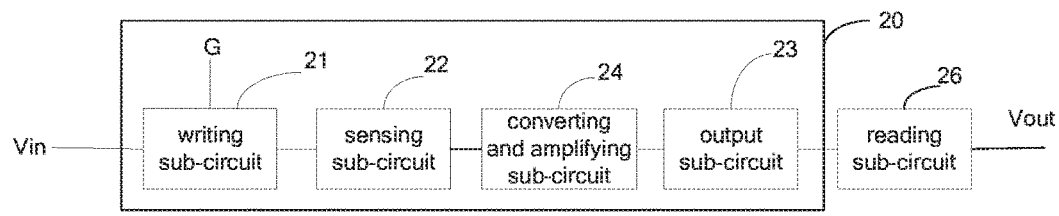
FIG. 3a a principle block diagram of a fingerprint identification sub-circuit of a fingerprint identification circuit provided by an embodiment of the present disclosure.
Figure 3B:
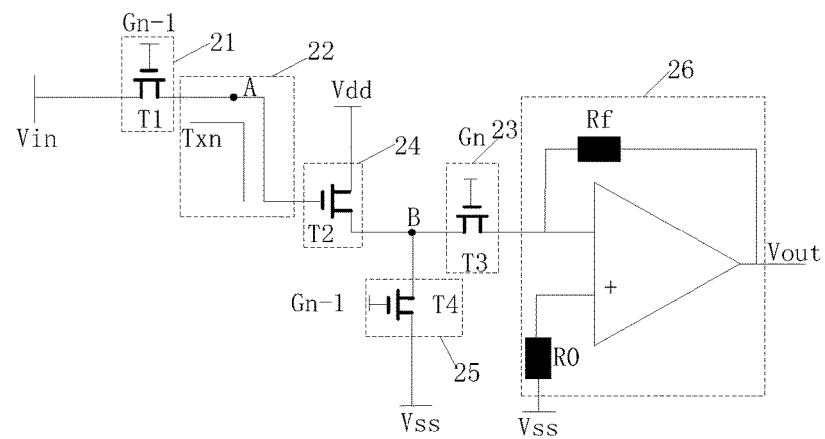
Figure 4:
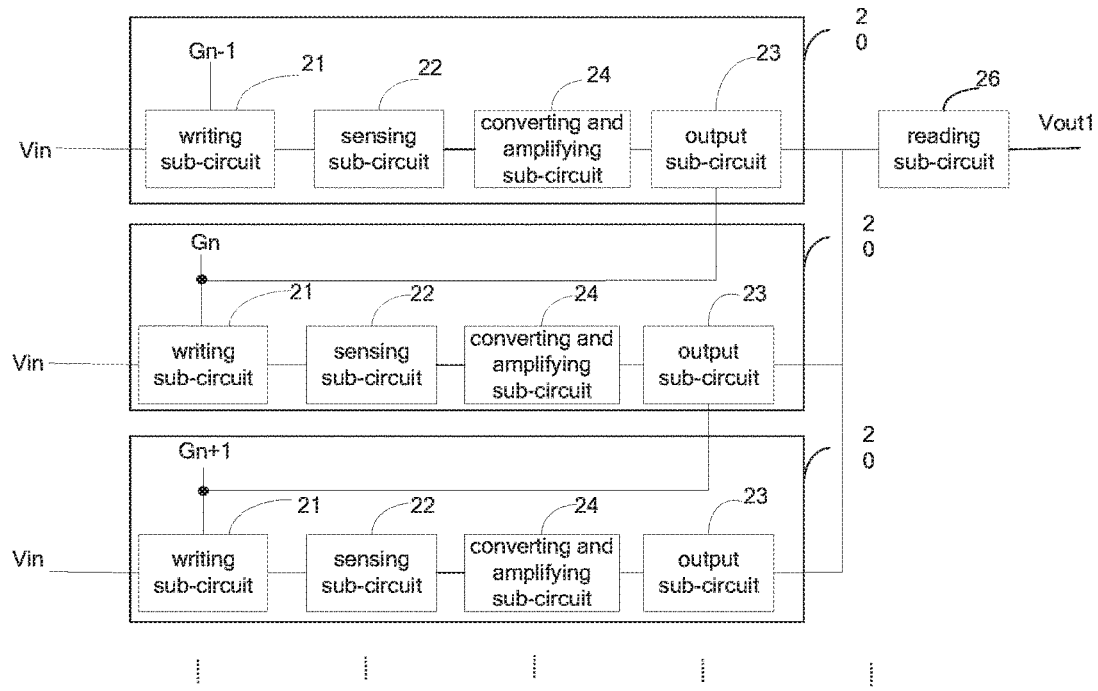
FIG. 4 is a partially schematic diagram of the fingerprint identification circuit provided by the embodiment of the present disclosure.

FIG. 3a a principle block diagram of a fingerprint identification sub-circuit of a fingerprint identification circuit provided by an embodiment of the present disclosure, FIG. 3b is a specific circuit diagram of a fingerprint identification sub-circuit shown in FIG. 3a, and FIG. 4 is a partially schematic diagram of the fingerprint identification circuit provided by the embodiment of the present disclosure. As shown in FIG. 4, this disclosure provides a fingerprint identification circuit, which comprises a plurality of reading sub-circuits 26 and a plurality of fingerprint identification sub-circuits 20, the fingerprint identification sub-circuits 20 are arranged in a matrix in rows and columns, wherein each column of fingerprint identification sub-circuits 20 are connected with one corresponding reading sub-circuit 26. Next, as shown in FIGS. 3a and 3b, each of the fingerprint identification sub-circuits 20 comprises a writing sub-circuit 21, a sensing sub-circuit 22, a converting and amplifying sub-circuit 24 and an output sub-circuit 23 connected in sequence. A control terminal of the writing sub-circuit 21 is connected with a scan signal input terminal G and is turned on upon an active signal is input to the scan signal input terminal G so as to write a detection signal to the sensing sub-circuit 22. The sensing sub-circuit 22 is configured to sense a fingerprint and transmits the obtained sensing signal to the converting and amplifying sub-circuit 24, the converting and amplifying sub-circuit 24 is configured to convert the sensing signal into a current signal, amplify the current signal by a preset multiples and then output it to the output sub-circuit 23. Furthermore, a corresponding reading sub-circuit 26 connected with the fingerprint identification sub-circuit 20 is connected with an output terminal of the output sub-circuit 23 and is configured to read the sensing signal from the output sub-circuit 23 and convert a current signal into a voltage signal to output.

The output sub-circuit 23 is configured to be turned on to output the sensing signal (which is a signal generated from the above detection signal by fingerprint sensing) when the writing sub-circuit 21 of the fingerprint identification sub-circuit where the output sub-circuit 23 is located is turned off, and to be turned off when the writing sub-circuit 21 of the fingerprint identification sub-circuit where the output sub-circuit 23 is located is turned on.

Optionally, a control terminal of an output sub-circuit of one fingerprint identification sub-circuit is connected with a control terminal of a writing sub-circuit of another fingerprint identification sub-circuit, for allowing the output sub-circuit of the one fingerprint identification sub-circuit and the writing sub-circuit of the another fingerprint identification sub-circuit to be turned on or off at the same time. As shown in FIG. 4, in an order from top to bottom, a control terminal of an output sub-circuit 23 of a first fingerprint identification sub-circuit 20 is connected with a control terminal of a writing sub-circuit 21 of a second fingerprint identification sub-circuit 20, thus when Gn is an active signal, the output sub-circuit 23 of the first fingerprint identification sub-circuit 20 and the writing sub-circuit 21 of the second fingerprint identification sub-circuit 20 are turned on at the same time. That is, as shown in FIG. 4, control terminals of output sub-circuits 23 of the (n−1)th row of fingerprint identification sub-circuits 20 are connected with a scanning signal inputting terminal Gn connected with the control terminals of the writing sub-circuits 21 of the nth row of fingerprint identification sub-circuits 20, thus, when Gn is an active signal, the output sub-circuits 23 of the (n−1)th row of fingerprint identification sub-circuits 20 and the writing sub-circuits 21 of the nth row of fingerprint identification sub-circuits 20 are turned on simultaneously.

That is to say, output of one fingerprint identification sub-circuit and turning on of the next fingerprint identification sub-circuit are performed at the same time, compared with the solution in which a fingerprint identification sub-circuit is turned on after a previous fingerprint identification sub-circuit outputs in the prior art, the present disclosure can reduce scanning time in the fingerprint identification procedure and thus the fingerprint identification efficiency can be increased.

Optionally, as shown in FIG. 3b, the writing sub-circuit 21 includes a first transistor T1, a gate of which, as a control terminal of the write sub-circuit 21, is connected with a scanning signal input terminal G, for controlling on and off of the writing sub-circuit 21. A first pole of the first transistor T1, as a signal input terminal of the writing sub-circuit 21, is connected to Vin, a second pole of the first transistor T1, as a signal output terminal of the writing sub-circuit 21, is connected with the sensing sub-circuit 22.

The sensing sub-circuit 22 includes: a first electrode A and a second electrode Txn provided oppositely, wherein the first electrode A is connected with a second electrode of the writing sub-circuit 21 and the signal input terminal of the converting and amplifying sub-circuit 24 respectively; the second electrode Txn is connected with a control signal terminal (which is not shown in drawings) for adjusting a preset multiples of the converting and amplifying sub-circuit 24 under the control of a control signal input from the control signal input terminal.

The converting and amplifying sub-circuit 24 includes: a second transistor T2, a gate of which serves as the signal input terminal of the converting and amplifying sub-circuit. A first electrode of the second transistor T2 is connected with a first level input terminal Vdd, a second electrode of the second transistor T2, as a signal output terminal of the converting and amplifying sub-circuit 24, is connected with the signal input terminal of the output sub-circuit 23.

The output sub-circuit 23 comprises a third transistor T3, a gate of which is configured as a control terminal of the output sub-circuit 23 for controlling on or off of the output sub-circuit 23; a first electrode of which serves as a signal input terminal of the output sub-circuit 23; and a second electrode of which serves as an output terminal of the output sub-circuit 23.

Figure 2A:
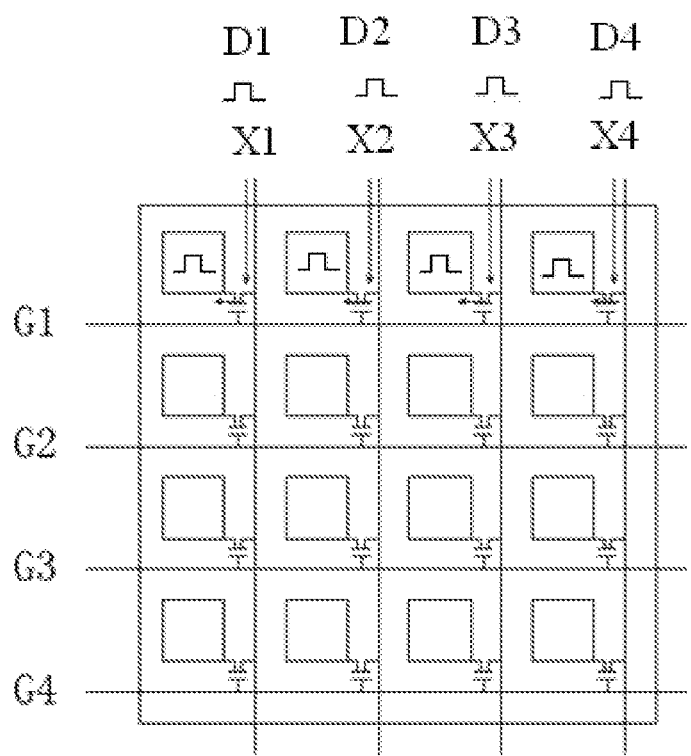
FIG. 2a is a schematic diagram of capacitance and voltage of the first row of sensing electrodes of the fingerprint identification circuit shown in FIG. 1 during a detection signal writing stage.
Figure 2B:
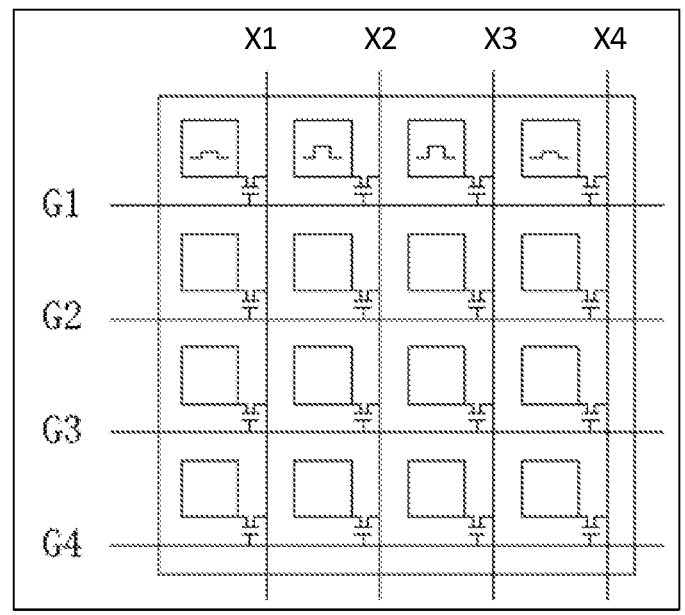
FIG. 2b is a schematic diagram of capacitance and voltage of the first row of sensing electrodes of the fingerprint identification circuit shown in FIG. 1 during a fingerprint sensing stage.
Figure 2C:
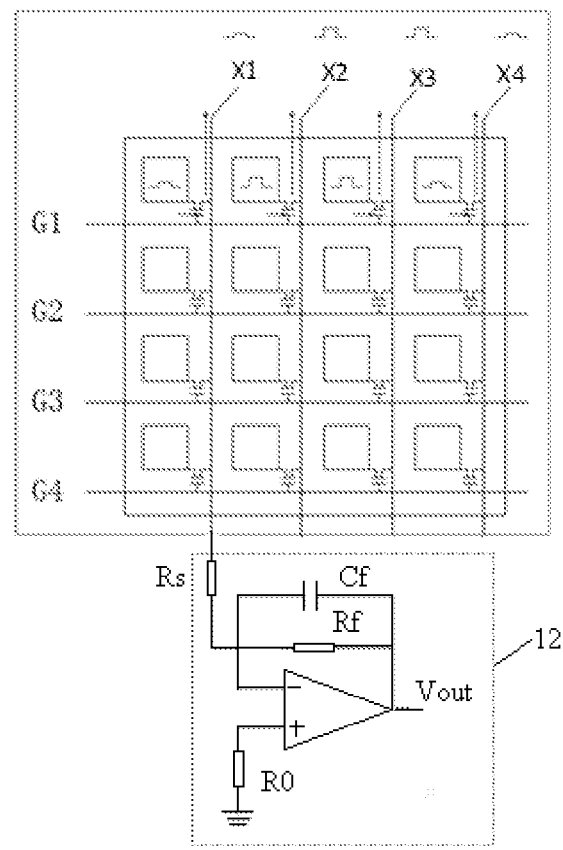
FIG. 2c is a schematic diagram of a fingerprint identification circuit comprising a reading sub-circuit in the prior art.

The reading sub-circuit 26 comprises: an operation amplifier, an inverse input terminal of which is connected with the signal output terminal of the output sub-circuit 23, wherein a pure resistance sub-circuit Rf is connected between the inverse input terminal and an output terminal of the operation amplifier. Compared with the prior art shown in FIG. 2c, peaks and valleys of a fingerprint can be identified quickly without needing wait for integral processing time, the report rate and fluency are improved.

Optionally, each of the fingerprint identification sub-circuits 20 further comprises a reset sub-circuit 25, which is provided between the converting and amplifying sub-circuit 24 and the output sub-circuit 23, and is turned on upon the writing sub-circuit 21 is turned on so as to reset the input terminal of the output sub-circuit 23 to a low level. Thus, the input terminal and the output terminal of the output sub-circuit 23 are at the same level upon the output sub-circuit 23 is turned on, so as to avoid affecting on the sensing signal and thus avoid affecting on the fingerprint identification accuracy.

Specifically, the reset sub-circuit 25 comprises a fourth transistor T4, a gate of which is configured as a control terminal of the reset sub-circuit 25 and is connected to the scanning signal input terminal G for controlling on or off of the reset sub-circuit 25; a first electrode of which is connected with a second level input terminal Vss; and a second electrode of which, as a signal output terminal of the reset sub-circuit 25, is connected to the signal input terminal of the third transistor T3.

Figure 1:
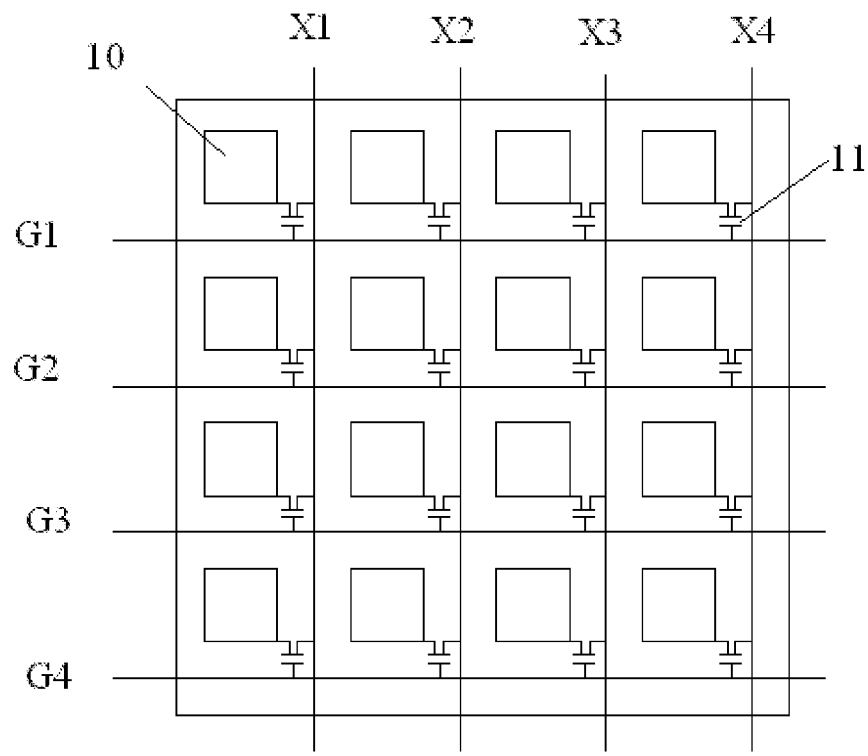
FIG. 1 is a schematic diagram of a fingerprint identification circuit in the prior art.

In a practical application, the plurality of fingerprint identification sub-circuits 20 of the fingerprint identification circuit may be provided in the following manner: the fingerprint identification sub-circuits 20 are arranged in a matrix in rows and columns, similar to FIG. 1, control terminals of the writing sub-circuits 21 of the fingerprint identification sub-circuits 20 in a same row are connected to a same scanning signal input terminal G, for controlling the writing sub-circuits 21 of the fingerprint identification sub-circuits 20 in the same row to be turned on simultaneously upon an active signal is input to the scanning signal input terminal G. Signal input terminals of the writing sub-circuits 21 of the fingerprint identification sub-circuits 20 in a same column are connected with a same signal line (that is, Vin, which is similar to the detection signal writing line X in FIG. 1). Signal output terminals of the output sub-circuits 23 of the fingerprint identification sub-circuits 20 in a same column are connected with a same reading sub-circuit 26, which is not connected with a signal line (detection signal writing line X) corresponding to this column, but is connected with the signal output terminals of the output sub-circuits 23.

Hereinafter, an operation procedure of a fingerprint identification circuit provided in an embodiment of the present disclosure will be described in detail in conjunction with FIG. 4 and FIG. 5a to FIG. 5c. The operation procedure includes the following stages.

(a) a detection signal writing stage: a driving voltage (which is an active signal when being at a high level) is applied to a scanning signal input terminal Gn−1, so that the first transistor T1 and the fourth transistor T4 of the first fingerprint identification sub-circuit 20 are turned on, at the same time, a detection signal is written, by Vin, to the first electrode A of the sensing sub-circuit 22 of the fingerprint identification sub-circuit 20, at this time, a voltage of the first electrode A is VA=Vin; the point B in FIG. 3b is reset so that the voltage of point B VB=Vss (ground).

(b) fingerprint sensing stage: when a finger touches the sensing sub-circuit 22, since the fingerprint texture includes two morphologies consisting of peaks and valleys and a distance between a peak and the sensing sub-circuit 22 is different from that between a valley and the sensing sub-circuit 22, therefore, so the influence of the peak on the capacitance of the sensing sub-circuit 22 corresponding thereto is different from that of the valley on the capacitance of the sensing sub-circuit 22 corresponding thereto.

Figure 5A:
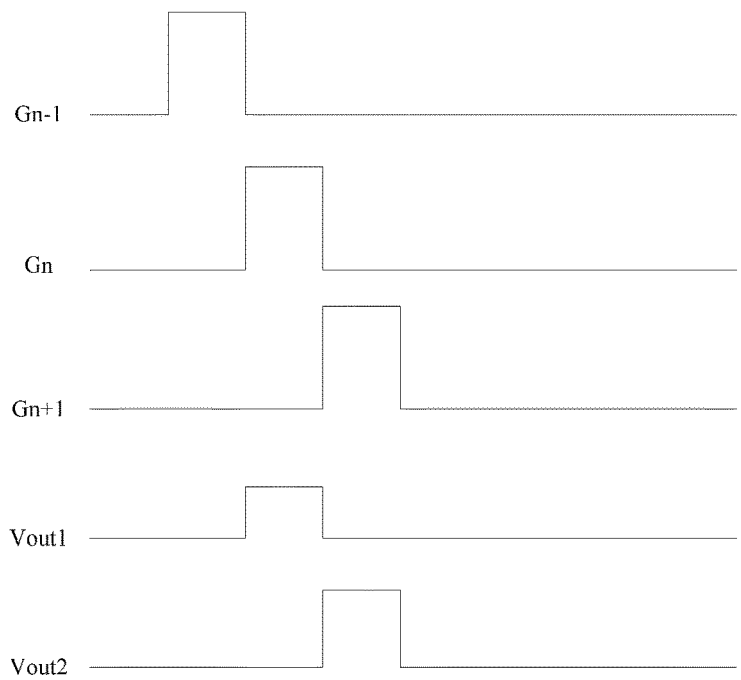
FIG. 5a is a sequence chart for fingerprint identification using the fingerprint identification circuit shown in FIG. 4.
Figure 5B:
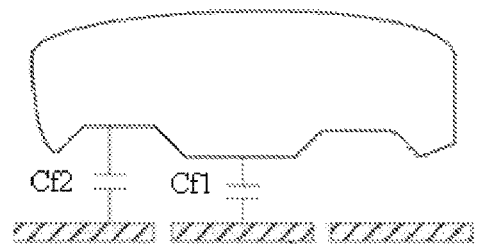
FIG. 5b is a schematic diagram of a capacitance formed between the fingerprint and the sensing sub-circuit when the fingerprint is sensed by using the fingerprint identification circuit shown in FIG. 3.
Figure 5C:
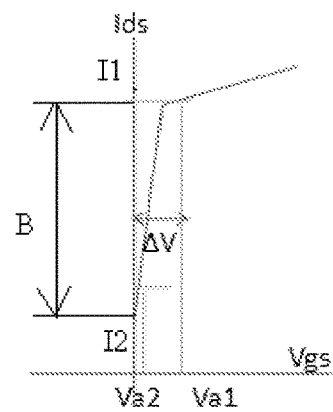
FIG. 5c is a schematic diagram of an Ids-Vgs curve relating to the embodiment of the present disclosure.

As shown in FIG. 5b, when touching, a capacitance Cf1 is generated between the peak and the sensing sub-circuit 22, a capacitance Cf2 is generated between the valley and the sensing sub-circuit 22, wherein, Cf1 is not the same as Cf2, Cf1 and Cf2 may change a mutual capacitance between the second electrode Txn and the first electrode A. Therefore, the sensing sub-circuit 22 may output various voltages correspondingly, for example, a peak corresponds to an output voltage Va1, and a valley corresponds to an output voltage Va2, wherein Va1 is not the same as Va2, thus ΔV=Va1−Va2. The second transistor T2 generates a current I1 by Va1, and generates a current I2 by Va2, the second electrode Txn is applied with a pulse control signal for adjusting an amplitude of a signal on the gate of the second transistor T2 so that ΔV is within a relatively large range, facilitating to distinguish a peak and a valley, that is, as shown in FIG. 5c, the range B of Ids is relatively large (for example, a ratio between I1 and I2 is large).

Certainly, in a case that a sum of a reset signal at the point B in FIG. 3b and a fingerprint sensing signal is within the range B of the Ids-Vgs curve, it is unnecessary to apply the pulse control signal to the second electrode Txn for adjusting, at this time, the second electrode Txn is applied with a DC source.

Txn may be the DC source, certainly, amplitude of the Txn may be an adjustable value, and may be positive or negative.

(c) signal reading stage: a reverse driving voltage is applied to the scanning signal input terminal Gn−1, so that the first transistor T1 and the fourth transistor T4 of the first fingerprint identification sub-circuit 20 are turned off, at the same time, a driving voltage is applied to a second scanning signal input terminal Gn, so that the first transistor T1 and the fourth transistor T4 of the second fingerprint identification sub-circuit 20 are turned on, and at the same time, the third transistor T3 of the first fingerprint identification sub-circuit 20 is turned on, so that the sensing signal is transmitted to the reading sub-circuit 26 by the third transistor T3.

The reading sub-circuit 26 process the output currents I1 and I2 corresponding to the peaks and valleys, specifically, the reading sub-circuit corresponding the peak outputs a voltage Vout1=−I1*Rf, the reading sub-circuit corresponding the valley outputs a voltage Vout1=−I2*Rf, and a ration between the voltages is large, wherein Rf represents a value of a resistance Rf in the reading sub-circuit 26. Therefore, the peak and the valley can be easily distinguished and thus accuracy of the fingerprint identification can be increased.

(d) a comparison process stage: comparing the detection signal written in the step (a) with the sensing signal read in the step (c), and determining whether the fingerprint texture corresponding to a position where each of the sensing electrodes 10 is located is a peak or a valley based on the difference obtained by the comparison.

And so on, the above (a)~(d) are repeated, a second row of fingerprint identification sub-circuits 20, a third row of fingerprint identification sub-circuits 20, till to the last row of fingerprint identification sub-circuits 20 are scanned in turn, so as to determine whether the fingerprint texture corresponding to a position where each of the sensing electrodes 10 of the overall fingerprint identification circuit is located is a peak or a valley, so that the fingerprint can be identified.

It can be seen from above that, in the fingerprint identification circuit provided in this embodiment, a converting and amplifying sub-circuit is provided between the sensing sub-circuit and the output sub-circuit, for converting the sensing signal output from the sensing sub-circuit into a current signal, amplifying the current signal by a preset multiple and then outputting it to the output sub-circuit; and the sensing signal is read by the reading sub-circuit and the current signal is converted into a voltage signal to output, so that current signals output from the converting and amplifying sub-circuits corresponding to a peak and a valley of a fingerprint respectively are different significantly and thus the converted voltage signals output by the converting and amplifying sub-circuits are also different significantly, the peak and the valley can be easily distinguished and thus accuracy of the fingerprint identification can be increased. In addition, since in the output sub-circuit, a conventional integration circuit is replaced with a resistor, the integration time is saved and thus the detection speed is increased.

Second Embodiment

The present disclosure further provides a touch apparatus, which includes a fingerprint identification circuit, this fingerprint identification circuit is one provided in the above first embodiment. The fingerprint identification circuit may refer to the above first embodiment and will not be repeated herein.

Third Embodiment

This disclosure provide a fingerprint identification method, this fingerprint identification method may be applied to the fingerprint identification circuit in the above first embodiment. The fingerprint identification method provided in this embodiment of the present disclosure may comprise the following steps:

201: turning on a writing sub-circuit of a fingerprint identification sub-circuit to write a detection signal to a sensing sub-circuit of the fingerprint identification sub-circuit, and turning off the output sub-circuit of the fingerprint identification sub-circuit simultaneously;

202. after the writing sub-circuit completes the writing of the detection signal, the sensing sub-circuit senses a fingerprint, generates a sensing signal and transmits it to an output sub-circuit, and turns the output sub-circuit connected with the sensing sub-circuit on, the output sub-circuit, after being turned on, outputs the sensing signal sensed by the sensing sub-circuit.

The fingerprint identification method may further comprise: reading, by the reading sub-circuit, the sensing signal output by the output sub-circuit and converting the current signal into a voltage signal to output.

Optionally, the fingerprint identification method further comprises: resetting the input terminal of the output sub-circuit of the fingerprint identification sub-circuit to a low level upon the writing sub-circuit of the fingerprint identification sub-circuit writes the detection signal.

Optionally, turning on a writing sub-circuit of another fingerprint identification sub-circuit in a same column and next row with respect to the fingerprint identification sub-circuit, while the output sub-circuit of the fingerprint identification sub-circuit is turned on.

Realization principle of the fingerprint identification method is the same as that of the first embodiment, and may refer to the first embodiment and will not be repeated herein.

It should be understood that, the foregoing embodiments are only exemplary embodiments used for explaining the principle of the present invention, but the present invention is not limited thereto. Various variations and improvements may be made by a person skilled in the art without departing from the protection scope of the present invention, and these variations and improvements also fall into the protection scope of the present invention.

The invention claimed is:

1. A fingerprint identification circuit, comprising a plurality of reading sub-circuits, and a plurality of fingerprint identification sub-circuits arranged in rows and columns, wherein each column of fingerprint identification sub-circuits are connected with one of the reading sub-circuits, each of the fingerprint identification sub-circuits comprises a writing sub-circuit, a sensing sub-circuit and a output sub-circuit connected in sequence, a control terminal of the writing sub-circuit is connected with a scan signal input terminal and is turned on upon an active signal is input to the scan signal input terminal so as to write a detection signal to the sensing sub-circuit; the sensing sub-circuit senses a fingerprint and transmits an obtained sensing signal to the output sub-circuit, the output sub-circuit is turned on and outputs the sensing signal upon the writing sub-circuit is turned off, and is turned off upon the writing sub-circuit is turned on, and wherein each of the fingerprint identification sub-circuits further comprising:

a converting and amplifying sub-circuit, which is provided between the sensing sub-circuit and the output sub-circuit, for converting the sensing signal output from the sensing sub-circuit into a current signal, amplifying the current signal by a preset multiple and then outputting it to the output sub-circuit, wherein the reading sub-circuit is connected with an output terminal of the output sub-circuit, and is configured to read the sensing signal output from the output sub-circuit and convert the current signal into a voltage signal to output.

2. The fingerprint identification circuit of claim 1, wherein each of the fingerprint identification sub-circuits further comprises a reset sub-circuit, which is provided between an output terminal of the converting and amplifying sub-circuit and an input terminal of the output sub-circuit, and is turned on upon the writing sub-circuit is turned on so as to reset the input terminal of the output sub-circuit to a low level.

3. The fingerprint identification circuit of claim 1, wherein a control terminal of the output sub-circuit of one of the fingerprint identification sub-circuits is connected with the control terminal of the writing sub-circuit of another one of the fingerprint identification sub-circuits in a same column and next row with respect to the one of the fingerprint identification sub-circuits, so that the output sub-circuit of the one of the fingerprint identification sub-circuits and the writing sub-circuit of the another one of the fingerprint identification sub-circuits are turned on or turned off simultaneously.

4. The fingerprint identification circuit of claim 1, wherein control terminals of the writing sub-circuits of the fingerprint identification sub-circuits in a same row is connected to a same scan signal input terminal, so that the writing sub-circuits of the fingerprint identification sub-circuits in the same row are turned on simultaneously upon an active signal is applied to the scan signal input terminal, and input terminals of the writing sub-circuits of the fingerprint identification sub-circuits in a same column are connected with a same signal line.

5. The fingerprint identification circuit of claim 1, wherein each of the reading sub-circuits comprises:

an operation amplifier, an inverse input terminal of which is connected with the output terminal of the output sub-circuit, wherein a pure resistance sub-circuit is connected between the inverse input terminal and an output terminal of the operation amplifier.

6. The fingerprint identification circuit of claim 5, wherein the writing sub-circuit comprises: a first transistor, a gate of which is configured as a control terminal of the writing sub-circuit for controlling on or off of the writing sub-circuit, a first pole of which is configured as an input terminal of the writing sub-circuit, and a second pole of which is configured as an output terminal of the writing sub-circuit.

7. The fingerprint identification circuit of claim 6, wherein the sensing sub-circuit comprises: a first electrode and a second electrode provided oppositely, wherein
the first electrode is connected with the writing sub-circuit and the converting and amplifying sub-circuit respectively;
the second electrode is connected with the control signal terminal, wherein the control signal terminal is configured to input a control signal to adjust the preset multiple of the converting and amplifying sub-circuit.

8. The fingerprint identification circuit of claim 7, wherein the converting and amplifying sub-circuit comprises: a second transistor, a gate of which is configured as an input terminal of the converting and amplifying sub-circuit, a first electrode of which is connected with a first level input terminal, and a second electrode of which is configured as an output terminal of the converting and amplifying sub-circuit.

9. The fingerprint identification circuit of claim 8, wherein the output sub-circuit comprises a third transistor, a gate of which is configured as a control terminal of the output sub-circuit for controlling on or off of the output sub-circuit; a first electrode of which is configured as a signal input terminal of the output sub-circuit and is connected with the signal output terminal of the converting and amplifying sub-circuit; and a second electrode of which is configured as an output terminal of the output sub-circuit.

10. The fingerprint identification circuit of claim 2, wherein the reset sub-circuit comprises a fourth transistor, a gate of which is configured as a control terminal of the reset sub-circuit for controlling on or off of the reset sub-circuit; a first electrode of which is connected with a second level input terminal; and a second electrode of which is configured as an output terminal of the reset sub-circuit and is connected to the input terminal of the output sub-circuit.

11. A touch apparatus, comprising a fingerprint identification circuit of claim 1.

12. A touch apparatus, comprising a fingerprint identification circuit of claim 2.

13. A touch apparatus, comprising a fingerprint identification circuit of claim 3.

14. A touch apparatus, comprising a fingerprint identification circuit of claim 4.

15. A touch apparatus, comprising a fingerprint identification circuit of claim 5.

16. A touch apparatus, comprising a fingerprint identification circuit of claim 6.

17. A touch apparatus, comprising a fingerprint identification circuit of claim 7.

18. A fingerprint identification method using the fingerprint identification circuit of claim 1, the fingerprint identification method comprises:
turning on a writing sub-circuit of a fingerprint identification sub-circuit to write a detection signal to a sensing sub-circuit of the fingerprint identification sub-circuit, and turning off the output sub-circuit of the fingerprint identification sub-circuit simultaneously;
after the writing sub-circuit completes the writing of the detection signal, the sensing sub-circuit senses a fingerprint, generates a sensing signal, and converts the sensing signal into a current signal and amplifies it by a preset multiple, and turning on an output sub-circuit connected with the sensing sub-circuit, the output sub-circuit, after being turned on, outputs the sensing signal sensed by the sensing sub-circuit; and
reading, by the reading sub-circuit, the sensing signal output by the output sub-circuit and converting the current signal into a voltage signal to output, turning on a writing sub-circuit of a fingerprint identification sub-circuit to write a detection signal to a sensing sub-circuit of the fingerprint identification sub-circuit, and turning off the output sub-circuit of the fingerprint identification sub-circuit simultaneously;
after the writing sub-circuit completes the writing of the detection signal, the sensing sub-circuit senses a fingerprint, generates a sensing signal, and converts the sensing signal into a current signal and amplifies it by a preset multiple, and turning on an output sub-circuit connected with the sensing sub-circuit, the output sub-circuit, after being turned on, outputs the sensing signal sensed by the sensing sub-circuit; and
reading, by the reading sub-circuit, the sensing signal output by the output sub-circuit and converting the current signal into a voltage signal to output.

19. The fingerprint identification method of claim 18, further comprising: resetting the input terminal of the output sub-circuit of the fingerprint identification sub-circuit to a low level upon the writing sub-circuit of the fingerprint identification sub-circuit writes the detection signal.

20. The fingerprint identification method of claim 18, further comprising:
turning on the writing sub-circuit of another one of the fingerprint identification sub-circuits in a same column and next row with respect to the fingerprint identification sub-circuit, while the output sub-circuit of the fingerprint identification sub-circuit is turned on.

* * * * *